United States Patent [19]

Moon et al.

[11] Patent Number: 5,225,567
[45] Date of Patent: Jul. 6, 1993

[54] HETEROCYCLIC ACETYLENIC AMINES HAVING CENTRAL NERVOUS SYSTEM ACTIVITY

[75] Inventors: Malcolm W. Moon; Richard F. Heier, both of Kalamazoo, Mich.

[73] Assignee: The Upjohn Company, Kalamazoo, Mich.

[21] Appl. No.: 923,107

[22] Filed: Jul. 30, 1992

Related U.S. Application Data

[60] Division of Ser. No. 853,671, Mar. 19, 1992, Pat. No. 5,157,124, which is a division of Ser. No. 675,891, Apr. 5, 1991, Pat. No. 5,137,905, which is a continuation-in-part of Ser. No. 263,692, Oct. 27, 1988, abandoned.

[51] Int. Cl.$^5$ .................. C07D 207/09; C07D 401/06; C07D 403/06; A61K 31/40
[52] U.S. Cl. ..................... 548/518; 548/531; 548/538; 548/546; 548/566; 548/569; 546/208
[58] Field of Search ................ 546/208; 548/518, 531, 548/538, 546, 566, 569

[56] References Cited

U.S. PATENT DOCUMENTS

| | | | |
|---|---|---|---|
| 2,867,620 | 1/1959 | Biel | 546/208 |
| 2,937,185 | 5/1960 | Biel | 546/208 |
| 3,334,115 | 8/1967 | Arnold et al. | 548/320 |
| 3,354,178 | 11/1967 | Dickinson | 546/208 |
| 3,925,411 | 12/1975 | Dahlbom et al. | 548/524 |
| 3,959,311 | 5/1976 | Dahlbom et al. | 546/2z |
| 5,001,142 | 3/1991 | Trybulski et al. | 514/584 |

OTHER PUBLICATIONS

B. Ringdahl, "5-Methyl-2-pyrrolidone Analogues of Oxotremorine as Selective Muscarinic Agonists," Journal of Medicinal Chemistry, 31, pp. 683–688 (1988).
B. M. Nilsson, et al., "Derivatives of the Muscarinic Agent N-Methyl-N-(1-methyl-4-pyrrolidino-2-butynyl)acetamide," Journal of Medicinal Chemistry, 31, pp. 577–582 (1988).
Chemical Abstracts, vol. 62, entry 2155(b) (1965).

Primary Examiner—Mary C. Lee
Assistant Examiner—Lenora A. Miltenberger
Attorney, Agent, or Firm—Donald Correglio

[57] ABSTRACT

Heterocyclic acetylenic amine compounds having the following structural formula

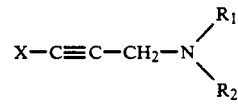

where X is

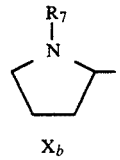

having cholinergic agonist or antagonist activity useful in the treatment of mental disorders, extrapyramidal motor disorders, disorders of the parasympathetic nervous system and glaucoma or as analgesics for the treatment of pain. Typical central nervous system disorders for which the subject compounds can be used include cognitive disorders of all ages, including senile dementia, Alzheimer's disease and other related disorders. The compounds are particularly developed to improve mental performance when a mental deficiency is diagnosed.

3 Claims, No Drawings

HETEROCYCLIC ACETYLENIC AMINES HAVING CENTRAL NERVOUS SYSTEM ACTIVITY

CROSS-REFERENCE TO RELATED APPLICATIONS

This application is a divisional of U.S. Ser. No. 07/853,671, filed Mar. 19, 1992, now U.S. Pat. No. 5,157,124, which was a divisional of U.S. Ser. No. 07/675,891, filed Apr. 5, 1991, now U.S. Pat. No. 5,137,905, which was the national phase of application PCT/US89/03596, filed Aug. 25, 1989, which was a continuation-in-part of U.S. Ser. No. 07/263,672, filed Oct. 27, 1988, abandoned.

BACKGROUND OF THE INVENTION

The present invention is directed toward heterocyclic acetylenic amine compounds having central nervous system activity. The compounds exhibit cholinergic activity and are particularly useful for improving mental performance or treating mental deficiencies. As an example, Alzheimer's disease is a cognitive disorder characterized in part by a significant reduction in choline acetyltransferase activity, high affinity choline uptake and synthesis of acetylcholine in the forebrain areas which receive cholinergic input. The reduction in presynaptic markers of the forebrain cholinergic neurons is due to the degeneration of these neuronal pathways. Clinical observations indicate that the central cholinergic system may be involved in the physiology of cognitive functions. Thus there is a medical need for a cholinergic agonist which is likely to have therapeutic efficacy in cognitive disorders. Cholinergic agonists can also be useful as analgesics to treat pain.

Those compounds having cholinergic antagonist activity are useful in the treatment of extrapyramidal motor disorders. The central nervous system activity of the compounds also indicates that they can be useful in the treatment of disorders of the parasympathetic nervous system.

These compounds are related to the cholinergic agonist oxotremorine 1-[4-(1-pyrrolidinyl-2-butynyl)-2-pyrrolidinone], which induces tremors and spasticity in laboratory animals by a cholinergic mechanism at extremely low doses. These undersirable side effects prevent the use of oxotremorine as a drug, and considerable effort has been directed to the preparation of related, clinically useful cholinergic agonists and antagonists.

DESCRIPTION OF RELATED ART

U.S. Pat. No. 3,925,411 discloses an oxotremorine antagonist N-(5-pyrrolidino-3-pentynyl)-pyrrolidin-2-one which is reported to have an increased half life over prior oxotremorine compounds. U.S. Pat. No. 3,959,311 also discloses compounds related to oxotremorine which are agonists, partial agonists and antagonists on isolated guinea pig ileum. These compounds are reported to have greater potency and less side-effects (antagonizing peripheral cholinergic effects) than the prior art compounds. Despite the proliferation of oxotremorine-like compounds there has been a continuing need to find more effective and safe compounds for treating mental disorders, extrapyramidal motor disorders, disorders of the parasympathetic nervous system and glaucoma.

More recently, a series of acetylenic amine compounds have been developed and evaluated for potential value in treating neurological and psychiatric conditions. A series of N-(4-amino-2-butynyl)-5-methyl-2-pyrrolidones were reported in Ringdahl, B, "5-methyl-2-pyrrolidone Analogues of Oxotremorine as Selective Muscarinic Agonists, J. Med. Chem. 31, 683–688 (1988). Another series of tertiary and quaternary analogues of N-methyl-N-(1-methyl-4-pyrrolidino-2-butynyl) acetamide were reported to have central antimuscarinic activity as they antagonized oxotremorine-induced tremors in mice as reported in Nilsson, et. al., "Derivatives of the Muscarinic Agent N-methyl-N-(1-methyl-4-pyrrolidino-2-butynyl)acetamide", J. Med. Chem., 31, 577–582 (1988).

SUMMARY OF THE INVENTION

The present invention is directed toward a family of heterocyclic acetylenic amine compounds having central nervous system activity. The compounds are represented by structural Formula I shown on the Formula sheet below including therapeutically acceptable salts thereof wherein $R_1$ and $R_2$ are hydrogen, methyl, ethyl or joined to form an azetidine, pyrrolidine, piperidine or imidazole ring which can be substituted with a methyl or ethyl group and the heterocyclic group X is as shown on the Formula sheet wherein $R_3$ is hydrogen, methyl or ethyl; $R_4$ is hydrogen, $C_1$–$C_6$ alkyl, $C_2$–$C_6$ alkenyl or $C_2$–$C_6$ alkynyl, phenyl, $C_1$–$C_6$ alkylcarbonyl or $C_1$–$C_6$ alkoxycarbonyl; $R_5$ and $R_6$ are hydrogen, methyl, ethyl or, together with the attached carbon atom, form a carbonyl group; n is 0 or 1, wherein n is 0 then a single or double bond is formed; and $R_7$ is hydrogen, $C_1$–$C_6$ alkyl, $C_1$–$C_6$ alkylcarbonyl, $C_1$–$C_6$ alkoxycarbonyl, aminocarbonyl, $C_1$–$C_6$ alkylaminocarbonyl, di-$C_1$–$C_6$ alkylaminocarbonyl or cyano.

Examples of "$C_1$–$C_6$" alkyl are methyl, ethyl, propyl, butyl, pentyl and hexyl and isomeric forms thereof.

Examples of "alkenyl" groups are straight or branched unsaturated hydrocarbons having at least one double bond such as ethenyl or propenyl.

Examples of "alkynyl" groups are straight or branched unsaturated hydrocarbons having at least one triple bond such as ethynyl or propynyl.

Examples of an "alkylcarbonyl" are acetyl, propionyl or isobutyryl.

Examples of "alkoxycarbonyl" groups are methoxycarbonyl, ethoxycarbonyl and t-butoxycarbonyl.

Examples of "alkylaminocarbonyl" are methylaminocarbonyl or propylaminocarbonyl and of "diakylaminocarbonyl" are dimethylaminocarbonyl or diethylaminocarbonyl.

Therapeutically acceptable salts are hydrochloride, hydrobromide, hydroiodide, sulfate, phosphate, acetate, propionate, lactate, maleate, malate, succinate, tartrate, cyclohexanesulfamates, methanesulfonates, ethanesulfonates, benzenesulfonates, toluenesulfonates and other pharmaceutically acceptable counter ions for amines. Additionally, the compounds of this invention may be administered in a suitable hydrated form.

The invention further provides a method for improving mental performance, treating pain, extrapyramidal motor disorders, glaucoma or parasympathetic nervous system disorders by administering a pharmaceutically effective amount of the subject compound.

DETAILED DESCRIPTION OF THE INVENTION

The new compounds of the present invention are structurally depicted by Formula I wherein $R_1$ and $R_2$ are hydrogen, methyl, ethyl or joined to form an azetidine, pyrrolidine, piperidine or imidazole ring which can be substituted with a methyl or ethyl group; and the heterocyclic group X is as shown on the formula sheet wherein;

$R_3$ is hydrogen, methyl or ethyl; $R_4$ is hydrogen, $C_1-C_6$ alkyl, $C_1-C_6$ alkenyl or $C_2-C_6$ alkynyl, phenyl, $C_1-C_6$ alkylcarbonyl or $C_1-C_6$ alkoxycarbonyl; $R_5$ and $R_6$ are hydrogen, methyl, ethyl or a carbonyl (formed from the attached carbon atom); n is 0 or 1, wherein n is 0 then a single or double bond is formed; and $R_7$ is hydrogen, $C_1-C_6$ alkyl, $C_1-C_6$ alkylcarbonyl, $C_1-C_6$ alkoxycarbonyl, aminocarbonyl, $C_1-C_6$ alkylaminocarbonyl, di-$C_1-C_6$ alkylaminocarbonyl or cyano.

A series of heterocyclic acetylenic amines generically disclosed in Formula I can be prepared by the procedures outlined in the attached Schemes to form the more specific structures as shown in the attached Tables.

Compounds of Structure i, were prepared from 1-(2-propynyl)-2-imidazolidinone intermediates which are prepared by any of the four procedures outlined in Scheme 1 as shown on the Scheme sheets below.

1-(2-propynyl)-2-imidazolidinone (II) was prepared by alkylation of the sodium salt of 2-imidazolidinone with propargyl bromide (method A) or, more conveniently, by reaction of propargyl amine with 2-chloroethyl isocyanate to give the urea III which was cyclized using sodium hydride (method B). 1-Alkyl-3-(2-propynyl)-2-imidazolidinones (IV) were prepared by reacting an N-alkylethylenediamine with carbonyldiimidazole followed by alkylation of the 1-alkyl-2-imidazolidinone product using sodium hydride/propargyl bromide (method C, Scheme 1). 1-(Carboalkoxy)-substituted intermediates were prepared as outlined in method D, Scheme 1 for the preparation of t-butyl 2-oxo-3-[4-(1-pyrrolidinyl)-2-butynyl]-1-imidazolidinecarboxylate (VI). t-Butoxycarbonyl β-alanine was reacted with diazabicycloundecene and diphenylphosphoryl azide to give V which was alkylated to give VI.

The 1,3-dihydro-1-(2-propynyl)-2H-imidazol-2-one intermediates were prepared as outlined in Scheme 2 for the synthesis of 1,3-dihydro-1-methyl-3-(2-propynyl)-2H-imidazol-2-one (X). Aminoacetaldehyde diethyl acetal was reacted with propargylbromide to give a mixture of the tertiary and secondary amines VII and VIII which were separated by chromatography on silica gel. Treatment of VIII with methyl isocyanate gave IX and this was heated in aqueous oxalic acid to give 1-methyl-3-(2-propynyl)-2H-imidazol-2-one (X).

Imidazolidinedione and tetrahydropyrimidinone intermediates were prepared by similar procedures. Alkylation of 1-(2-propynyl)-2,4-imidazolidinedione with methyl iodide afforded 3-methyl-1-(2-propynyl)-2,4-imidazolidinedione. Alkylation of 1-methyl-2,4-imidazolidinedione with propargyl bromide afforded 1-methyl-3-(2-propynyl)-2,4-imidazolidinedione. N-methyl 1,3-propanediamine was converted to tetrahydro-1-methyl-2(1H)-pyrimidinone using the procedure of Scheme I (method C).

The intermediate imidazolidinones and imidazolones were converted to the final products using the general procedures outlined in Scheme 2. 1,3-dihydro-1-methyl-3-(2-propynyl)-2H-imidazol-2-one was reacted with paraformaldehyde and pyrrolidine in dioxane using cuprous chloride as catalyst to give 1,3-dihydro-1-methyl-3-[4-(1-pyrrolidinyl)-2-butynyl]-2H-imidazol-2-one.

The diethylamine analogue was prepared similarly and was reacted with cyanogen bromide to give the bromide XI which was reacted with imidazole to give 1,3-dihydro-1-[4-(1H-imidazol-1-yl)-2-butynyl]-3-methyl-2H-imidazol-2-one and with 1-acetyl-4-methylimidazole to give XII which was hydrolyzed to 1,3-dihydro-1-methyl-3-[4-(5-methyl-1H-imidazol-1-yl)-2-butynyl]-2H-imidazol-2-one. The imidazolidinone analogues of Table 1, imidazolones of Table 2 and imidazolidinedione and tetrahydropyrimidinones of Table 3 were prepared by these general procedures.

The cyclic analogues were prepared from (R)-prolinol as outlined in Scheme 3. (R)-prolinol was reacted with di-t-butyl dicarbonate to give compound XIII, which was converted to aldehyde XIV under Swern oxidation conditions. Further reaction of the aldehyde with carbon tetrabromide/triphenylphosphine afforded the dibromo alkene XV which was treated with 3 equivalents of butyl lithium to give the acetylene XVI. This was reacted with paraformaldehyde and pyrrolidine in presence of cuprous chloride as catalyst to give (R)-t-butyl 2-[3-(1-pyrrolidinyl)-1-propynyl]-1-pyrrolidinecarboxylate and this was treated with methanolic hydrogen chloride to give the diamine XVII. Acetylation of this diamine with acetic anhydride gave (R)-1-acetyl-2-[3-(1-pyrrolidinyl)-1-propynyl]pyrrolidine. Related products (see, Table 4) were prepared by treating the diamine with other acylating reagents.

A series of dimethylamine analogues were prepared by the same reaction sequence, by reacting XVI with paraformaldehyde and dimethylamine. The reaction sequence was repeated with (S)-prolinol to give the enantiomeric series of compounds (see, Table 5). These products can also be obtained in racemic form by the same reaction sequence using racemic 2-(hydroxymethyl)pyrrolidine (prolinol) as the starting material.

The compounds of the invention have central nervous system activity and therefore, are useful in the treatment of mental disorders such as senile dementia, Alzheimer's disease, schizophrenia, mania and depression, extrapyramidal motor disorders such as Parkinson's disease, Huntingtons chorea, tardive dyskensia, disorders of the parasympathetic nervous system such as post-operative abdominal distension, gastric atony, irritable colon syndrome, colitis diverticulitus, biliary colic, peptic ulcers, urine retention and renal colic, or glaucoma or as analgesics for the treatment of pain.

Compounds useful for improving mental performance are recognized as cholinergic agonists or partial agonists. These compounds can also be useful as analgesics and for the treatment of glaucoma. The agonists are easily identified from cholinergic receptor binding results by calculating the Ki ratios. Any compound having a Ki ratio of at least ten is considered an agonist or partial agonist and, therefore, a pharmeutical candidate for improved mental performance or as an analgesic. Whereas compounds having a Ki ratio less than ten are considered antagonist which are useful in the treatment of extrapyramidal motor disorders.

The activities of the new heterocyclic acetylenic amine compounds of structure i are shown in Tables 1, 2 and 3. The activities of compounds of structure ii are shown in Tables 4 and 5. The compounds numbers listed in the Tables correspond to the same Example number.

The pharmacological activity for each of the compounds prepared is reported on the respective Tables 1-5. The biological methods employed were as follows:

Cholinergic receptor binding data for each of the compounds was obtained using the tritiated ligands oxotremorine M and quinuclidine benzylate.

Oxotremorine antagonist assays were performed on groups of six mice weighing 18-22 g. Each was dosed intraperitoneally with the test compound prepared in 0.25% methylcellulose and were placed in individual cages. Twenty minutes later the mice were injected subcutaneously with 0.5 mg/kg of oxotremorine dissolved in saline. Ten minutes later the mice were scored for body tremor. Doses of the compound under study began at 100 mg/kg and were decreased at a 0.5 log interval until no responders were obtained. The procedure described by Spearman and Karber, Finney, D. J., "Statistical Methods in Biological Assay", Chapter 20, was used to calculate the $ED_{50}$ and 95% confidence intervals.

For determination of analgesic activity, the test compound was injected subcutaneously into a group of four $CF_1$ mice. Thirty minutes later the mice were injected i.p. with 0.15% HCl, 10 ml./kg. Mice were then placed in plastic boxes and observed for fifteen minutes to record the number of animals failing to writhe. If at least three of the mice receiving the test compound failed to writhe, the compound was retested at dose levels decreasing at 0.3 log intervals.

For antagonism of amnesia produced by scopolamine a one trial, step through passive avoidance paradigm was used. In this procedure a mouse was placed on a square platform adjoining a darkened chamber. The mouse could enter the chamber through a hole above the platform. Following placement on the platform, the mouse was enclosed by a clear plexiglas cover which mildly restricted movement, limiting the animal to turning around and partial rearing. A sliding door was opened after this, exposing the entrance to the chamber. A timer was started at the same time the door was opened, in order to record latency to enter the chamber. Upon complete entry into the darkened box, the door was closed behind the mouse and a 1 mA, 2 sec, direct current shock applied to the feet of the mouse through the grid floor. The mouse was immediately removed from the chamber and returned to a 24 hr group holding cage.

Drug testing involved intraperitoneal injection of the test compound followed 15 min later by subcutaneous injection of 1 mg/kg scopolamine hydrobromide. Training was then conducted 15 min following scopolamine injection. Mice were housed in group cages overnight and tested for retention 24 hrs after training. Test sessions were conducted exactly like training sessions, except that no drugs were administered before testing and no shock was given upon entry. The latency for each mouse to enter the chamber was recorded, with a cut-off at 180 sec.

Median group latencies to enter the chamber during both training and testing were recorded and a Wilcoxon rank sum test applied to data comparing the parallel "scopolamine only" group with all drug combination groups on testing. On training, comparisons were made between the "No Drug" group, which received saline prior to shock training, and each of the scopolamine and test compound combinations.

Of the compounds tested using this procedure, compound 36 was the most active.

The dosage regimen for treating patients with the compounds of this invention is selected in accordance with a variety of factors including the type, age, weight, sex, and medical condition of the patient, the severity of the psychosis, the route of administration and the particular compound employed. An ordinarily skilled physician or psychiatrist will readily determine and prescribe the effective amount of compound to prevent or arrest the progress of the condition. In so proceeding, the physician or psychiatrist could employ relatively low dosages at first, subsequently increasing the dose until a maximum response is obtained.

Initial dosages of the compounds of the invention are ordinarily in the area of at least 10 mg up to about 1200 mg per day orally, which may be given in a single dose or in multiple doses. When other forms of administration are employed equivalent doses are administered. When dosages beyond 600 mg are employed, care should be taken with each subsequent dose to monitor possible toxic effects.

The compounds of this invention are administered in oral unit dosage forms such as tablets, capsules, pills, powders, or granules. They may also be introduced parenterally, (e.g., subcutaneously, intravenously, or intramuscularly), using forms known to the pharmaceutical art. They also may be administered rectally or vaginally in such forms as suppositories or bougies. In general, the preferred route of administration is oral.

The compounds of this invention can also be administered as therapeutically acceptable salt such as hydrochloride, hydrobromide, hydroiodide, sulfate, phosphate, acetate, propionate, lactate, maleate, malate, succinate, tartrate, cyclohexanesulfamates, methanesulfonates, ethanesulfonates, benzenesulfonates, toluenesulfonates and the like. Additionally, the compounds of this invention may be administered in a suitable hydrated form.

EXAMPLE 1

1-Methyl-3-[4-(1-pyrrolidinyl)-2-butynyl]-2-imidazolidinone

Part A. 1-Methyl-3-(2-propynyl)-2-imidazolidinone.

Solutions of N-methylethylenediamine (11.3 g, 0.15 mol) in DMF (60 mL) and carbonyldiimidazole (24.3 g, 0.015 mol) in DMF (120 mL) were added at an equimolar rate over a 20 min period to DMF (30 mL) at 70° C. The solution was then cooled, the DMF was removed under reduced pressure, and the residual solid was chromatographed on silica gel to give 6.9 g of 1-methyl-2-imidazolidinone. The product was crystallized from ethyl acetate to give 5.7 g, mp 113°-116° C.

A suspension of potassium hydride (10.44 g of a 35% by wt suspension in mineral oil, washed with ether to remove oil, 0.09 mol) in dry THF (50 mL) was added dropwise, with cooling, to a stirred solution of 1-methyl-2-imidazolidinone (7.6 g, 0.076 mol) in dry THF (150 mL). After warming to room temperature and stirring for 20 min, the reaction was cooled again and propargyl bromide (13.54 g of an 80% solution in toluene, 0.09 mol) was added dropwise. The reaction was then allowed to slowly warm to room temperature and was stirred for 0.5 hr. The reaction was quenched with methanol and water and the solvents were removed under reduced pressure. The residual oil was partitioned between ethyl acetate and water; evaporation of the organic phase gave 10.65 g crude product. The compound was purified by chromatography on silica gel in chloroform to get 4.51 g of crystalline product.

Part B. 1-Methyl-3-[4-(1-pyrrolidinyl)-2-butynyl]-2-imidazolidinone.

A mixture of 1-methyl-3-(2-propynyl)-2-imidazolidinone (2.3 g, 0.017 mol), pyrrolidine (1.30 g, 0.018 mol), ground paraformaldehyde (0.55 g, 0.018 mol), and cuprous chloride (0.022 g) in dioxane (20 mL) was stirred at 55° C. for 6 hr and cooled to room temperature. The solvent was removed under reduced pressure and the crude product was partitioned between ethyl acetate and water. Evaporation of the ethyl acetate gave 3.63 g crude product. The compound was purified by chromatography on silica gel in chloroform to give 2.77 g (75%) of pure product as a liquid.

This product (2.67 g) was mixed with anhydrous oxalic acid (1.08 g). Crystallization from methanol:ether gave 1.5 g of oxalate salt, m.p. 91°–93° C. Recrystallization from the same solvents gave 1.2 g white crystals, m.p. 94°–96° C.

Anal. Calcd for $C_{12}H_{19}N_3O.C_2H_2O_4$: C, 54.01; H, 6.80; N, 13.50. Found: C, 54.14; H, 6.89; N, 13.52.

EXAMPLE 2

1-(2-Propynyl)-2-imidazolidinone

Method A (Scheme 1)

Sodium hydride (5.76 g of a 50% oil dispersion, 0.12 mol) was added to a suspension of imidazolidinone (17.22 g, 0.2 mol) in dry THF (500 mL) and refluxed for 3 hr. The reaction was then cooled and propargyl bromide (14.84 g, 0.1 mol) was added. This mixture was refluxed for an additional 2.5 h, cooled, and filtered. The solvent was removed to give 21.41 g of a mixture of the mono- and bis-substituted propynyl adducts. The product was chromatographed on silica gel in chloroform to get 3.29 g of 1,3-bis-(2-propynyl)-2-imidazolidinone which was crystallized from ethyl acetate/Skellysolve B to give 2.0 g white crystals, m.p. 100°–105° C. Recrystallization gave 1.54 g white crystals, m.p. 109°–112° C.

Anal. Calcd for $C_9H_{10}N_2O$: C, 66.65; H, 6.22; N, 17.27. Found: C, 66.19; H, 6.39; N, 17.50.

Continued elution of the column with 10% methanol:chloroform gave 3.33 g of 1-(2-propynyl)-2-imidazolidinone, m.p. 110°–115° C. which was recrystallized from ethyl acetate/Skellysolve B to get 2.89 g of material, m.p. 119°–123° C.

Anal. Calcd for $C_6H_8N_2O$: C, 58.05; H, 6.50; N, 22.57. Found: C, 57.70; H, 6.69; N, 22.65.

Method B (Scheme 1)

Chloroethyl isocyanate (12.2 g, 0.11 mol) was added at 0° C. to a stirred solution of propargylamine (6.6 g, 0.12 mol) in THF (200 mL). The solution was allowed to warm to room temperature and sodium hydride (5.5 g of 50% in oil, washed with ether to remove the oil) was added. The reaction was quenched with acetic acid (6.0 mL), the THF was removed under reduced pressure, and the residue was partitioned between ethyl acetate and water. The ethyl acetate was evaporated and the residual solid was crystallized from ethyl acetate: Skellysolve B to give 11.1 g of 1-(2-propynyl)-2-imidazolidinone, m.p. 110°–115° C.

EXAMPLE 3

1,3-Dihydro-methyl-3-(2-propynyl)-2H-imidazol-2-one

Part A. 2,2-diethoxy-N-(2-propynyl)ethylamine

Propargyl bromide (14.7 g of 80% solution in toluene, 0.1 mol) was added to a stirred solution of aminoacetaldehyde diethyl acetal (13.3 g, 0.1 mol) in THF (200 mL). After 2 h the THF was removed and the residual oil was partitioned between ether and sodium hydroxide solution. Evaporation of the ether gave an oil which was chromatographed on silica gel to give 4.7 g of 2,2-diethoxy-N,N-bis-(2-propynyl)ethylamine and 8.1 g of 2,2-diethoxy-N-(2-propynyl)ethylamine.

Part B. 1,3-Dihydro-methyl-3-(2-propynyl)-2H-imidazol-2-one.

Methyl isocyanate (1.3 g, 0.02 mol) was added to a stirred solution of 2,2-diethoxy-N-(2-propynyl)ethylamine (3.4 g, 0.02 mol) in ether (50 mL). After 30 min the ether was evaporated and the residue was dissolved in water (50 mL), oxalic acid (1.7 g) was added, and the solution was heated at 50° C. for 30 min. The solution was then concentrated to 10 mL and neutralized with 4N NaOH solution, and extracted with ethyl acetate (4×50 mL). The ethyl acetate was evaporated and the residue was chromatographed on silica gel to give 2.1 g of product which was recrystallized from ethyl acetate:Skellysolve B; m.p. 69°–72° C.

Anal. Calcd for $C_7H_8N_2O$: C, 61.75; H, 5.92; N, 20.58. Found: C, 61.65; H, 5.93; N, 20.50.

EXAMPLE 4

1-[4-(Diethylamino)-2-butynyl]-1,3-dihydro-3-methyl-2H-imidazol-2-one

This product, a liquid, was prepared according to Example 1, Part B by substituting 1,3-dihydro-1-methyl-3-(2-propynyl)-2H-imidazol-2-one for 1-methyl-3-(2-propynyl)-2-imidazolidinone and diethylamine for pyrrolidine.

The bulk of the product was converted to the sesquioxalate salt; m.p. 111°–114° C.

Anal. Calcd for $C_{12}H_{19}N_3O.1\frac{1}{2}C_2H_2O_4$: C, 50.55; H, 6.22; N, 11.79. Found: C, 50.68; H, 6.32; N, 11.99.

EXAMPLE 5

1-(4-bromo-2-butynyl)-1,3-dihydro-3-methyl-2H-imidazol-2-one

Cyanogen bromide (6.0 g, 0.057 mol) was added to a stirred solution of 1-[4-(diethylamino)-2-butynyl]-1,3-dihydro-3-methyl-2H-imidazol-2-one in dioxane (130 mL). After evaporation of the dioxane, the residual oil was chromatographed on silica gel using chloroform:1% methanol as the eluant to give 10.8 g of 1-(4-bromo-2-butynyl)-1,3-dihydro-3-methyl-2H-imidazol-2-one as an oil.

EXAMPLE 6

1,3-Dihydro-1-[4-(1H-imidazol-1-yl)-2-butynyl]-3-methyl-2H-imidazol-2-one

Imidazole (3.87 g, 0.057 mol) was added to a stirred solution of 1-(4-bromo-2-butynyl)-1,3-dihydro-3-methyl-2H-imidazol-2-one (3.26 g, 0.014 mol) in dioxane (50 mL). After 18 hr the dioxane was evaporated and the residue was chromatographed on silica gel to give 2.4 g of product.

The bulk of the product was converted to the oxalate salt; m.p. 106°–109° C.

Anal. Calcd for $C_{11}H_{12}N_4O.C_2H_2O_4$: C, 50.98; H, 4.61; N, 18.29. Found: C, 50.42; H, 4.76; N, 17.88.

EXAMPLE 7

1,3-Dihydro-1-methyl-3-[4-(5-methyl-1H-imidazol-1-yl)-2-butynyl]-2H-imidazol-2-one A mixture of 1-(4-bromo-2-butynyl)-1,3-dihydro-3-methyl-2H-imidazol-2-one (4.12 g, 0.018 mol) and 1-acetyl-4-methylimidazole (4.47 g, 0.036 mol) in acetonitrile (6 mL) was heated in an oil bath (bath temperature 85° C.) for 1 hr. Methanol (20 mL) was added and, after 1 hr, the solvents were removed and the residue was partitioned between ethyl acetate and 4N NaOH solution. The ethyl acetate was removed and the residual oil was chromatographed on silica gel using methanol:chloroform as eluant to give 3.3 g of product.

The bulk of the product was converted to the methanesulfonate salt; m.p. 149°–153° C.

Anal. Calcd for $C_{12}H_{14}N_4O.CH_4O_3S$: C, 47.84; H, 5.56; N, 17.17; S, 9.82. Found: C, 47.62; H, 5.80; N, 17.27; S, 9.83.

EXAMPLE 8 t-Butyl 2-oxo-3-[4-(1-pyrrolidinyl)-2-butynyl]-1-imidazolidinecarboxylate

This product, a liquid, was prepared according to Example 1 by substituting 1-t-butoxycarbonyl-2-imidazolidinone for 1-methyl-2-imidazolidinone.

The bulk of the product was converted to the oxalate salt; m.p. 128°–30° C.

Anal. Calcd for $C_{16}H_{25}N_3O_3.C_2H_2O_4$: C, 54.40; H, 6.85; N, 10.57. Found: C, 54.21; H, 6.82; N, 10.65.

EXAMPLE 9

1-[4-(1-Pyrrolidinyl)-2-butynyl]-2-imidazolidinone

This product was prepared according to Example 1, Part B by substituting 1-(2-propynyl)-2-imidazolidinone for 1-methyl-3-(2-propynyl)-2-imidazolidinone. The compound was recrystallized from ethyl acetate:Skellysolve B; m.p. 71°–5° C.

Anal. Calcd for $C_{11}H_{17}N_3O$: C, 63.74; H, 8.27; N, 20.27. Found: C, 63.49; H, 8.14; N, 20.45.

EXAMPLE 10

1-[4-(1-Dimethylamino)-2-butynyl]-3-methyl-2-imidazolidinone

This product, a liquid, was prepared according to Example 1, Part B by substituting dimethylamine for pyrrolidine.

The bulk of the product was converted to the oxalate salt; m.p. 122°–25° C.

Anal. Calcd for $C_{10}H_{17}N_3O.C_2H_2O_4$: C, 50.52; H, 6.71; N, 14.73. Found: C, 50.33; H, 6.87; N, 14.44.

EXAMPLE 11 t-Butyl 3-[4-(dimethylamino)-2-butynyl]-2-oxo-1-imidazolidinecarboxylate

This product, a liquid, was prepared according to Example 1 by substituting dimethylamine for pyrrolidine and 1-t-butoxycarbonyl-2-imidazolidinone for 1-methyl-2-imidazolidinone.

The bulk of the product was converted to the oxalate salt; m.p. 134°–137° C.

Anal. Calcd for $C_{14}H_{23}N_3O_3.C_2H_2O_4$: C, 51.74; H, 6.79; N, 11.32. Found: C, 51.39; H, 6.89; N, 11.17.

EXAMPLE 12

4,4-Dimethyl-1-[4-(1-pyrrolidinyl)-2-butynyl]-2-imidazolidinone.

This product, a liquid, was prepared according to Example 1 by substituting 4,4-dimethyl-2-imidazolidinone for 1-methyl-2-imidazolidinone.

The bulk of the product was converted to the oxalate salt; m.p. 145°–148° C.

Anal. Calcd for $C_{13}H_{21}N_3O.C_2H_2O_4$: C, 55.37; H, 7.13; N, 12.92. Found: C, 55.62; H, 7.38; N, 12.96.

EXAMPLE 13

3,4,4-Trimethyl-1-[4-(1-pyrrolidinyl)-2-butynyl]-2-imidazolidinone

This product, a liquid, was prepared according to Example 1 by substituting 1,5,5-trimethyl-2-imidazolidinone for 1-methyl-2-imidazolidinone.

The bulk of the product was converted to the oxalate salt; m.p. 148°–150° C.

Anal. Calcd for $C_{14}H_{23}N_3O.C_2H_2O_4$: C, 56.45; H, 7.51; N, 12.37. Found: C, 56.62; H, 7.43; N, 12.38.

EXAMPLE 14

1-(2-Propynyl)-3-[4-(1-pyrrolidinyl)-2-butynyl]-2-imidazolidinone

This product, a liquid, was prepared according to Example 1, Part B by substituting 1,3-bis-(2-propynyl)-2-imidazolidinone for 1-methyl-3-(2-propynyl)-2-imidazolidinone.

EXAMPLE 15

4-Methyl-1-[4-(1-pyrrolidinyl)-2-butynyl]-2-imidazolidinone

This product, a liquid, was prepared according to Example 1 by substituting 4-methyl-2-imidazolidinone for 1-methyl-2-imidazolidinone.

The bulk of the product was converted to the oxalate salt; m.p. 151°–153° C.

Anal. Calcd for $C_{12}H_{19}N_3O.C_2H_2O_4$: C, 54.01; H, 6.80; N, 13.50. Found: C, 53.61; H, 7.00; N, 13.45.

EXAMPLE 16

5,5-Dimethyl-1-[4-(1-pyrrolidinyl)-2-butynyl]-2-imidazolidinone

This product was prepared according to Example 1, Part B by substituting 5,5-dimethyl-1-(2-propynyl)-2-imidazolidinone for 1-methyl-3-(2-propynyl)-2-imidazolidinone; m.p. 50° C.

Anal. Calcd for $C_{13}H_{21}N_3O$: C, 66.35; H, 9.00; N, 17.86. Found: C, 65.53; H, 8.94; N, 17.66.

The bulk of the product was converted to the oxalate salt; m.p. 121°–124° C.

Anal. Calcd for $C_{13}H_{21}N_3O.C_2H_2O_4$: C, 55.37; H, 7.12; N, 12.92. Found: C, 55.41; H, 7.14; N, 12.86.

EXAMPLE 17 t-Butyl 5-methyl-2-oxo-3-[4-(1-pyrrolidinyl)-2-butynyl]-1-imidazolidinecarboxylate This product, a liquid, was prepared according to Example 1 by substituting 1-t-butoxycarbonyl-5-methyl-2-imidazolidinone for 1-methyl-2-imidazolidinone.

The bulk of the product was converted to the oxalate salt; m.p. 148°–151° C.

Anal. Calcd for $C_{17}H_{27}N_3O_3 \cdot C_2H_2O_4$: C, 55.46; H, 7.10; N, 10.21. Found: C, 55.26; H, 7.19; N, 10.15.

EXAMPLE 18 t-Butyl 4-methyl-2-oxo-3-[4-(1-pyrrolidinyl)-2-butynyl]-1-imidazolidinecarboxylate This product, a liquid, was prepared according to Example 1, Part B by substituting 1-t-butoxycarbonyl-4-methyl-3-(2-propynyl)-2-imidazolidinone for 1-methyl-3-(2-propynyl)-2-imidazolidinone.

The bulk of the product was converted to the oxalate salt; m.p. 144°–146° C.

Anal. Calcd for $C_{17}H_{27}N_3O_3 \cdot C_2H_2O_4$: C, 55.46; H, 7.10; N, 10.21. Found: C, 55.40; H, 7.20; N, 10.26.

EXAMPLE 19

1,4-Dimethyl-3-[4-(1-pyrrolidinyl)-2-butynyl]-2-imidazolidinone

This product, a liquid, was prepared according to Example 1, Part B by substituting 1,4-dimethyl-3-(2-propynyl)-2-imidazolidinone for 1-methyl-3-(2-propynyl)-2-imidazolidinone.

The bulk of the product was converted to the oxalate salt; m.p. 80°–84° C.

Anal. Calcd for $C_{13}H_{21}N_3O \cdot C_2H_2O_4$: C, 55.37; H, 7.12; N, 12.92. Found: C, 54.46; H, 7.24; N, 12.60.

EXAMPLE 20

1-Phenyl-3-[4-(1-pyrrolidinyl)-2-butynyl]-2-imidazolidinone

This product, a liquid, was prepared according to Example 1, Part B by substituting 1-phenyl-3-(2-propynyl)-2-imidazolidinone for 1-methyl-3-(2-propynyl)-2-imidazolidinone.

The bulk of the product was converted to the oxalate salt; m.p. 138°–140° C.

Anal. Calcd for $C_{17}H_{21}N_3O \cdot C_2H_2O_4$: C, 61.11; H, 6.21; N, 11.25. Found: C, 61.06; H, 6.08; N, 11.50.

EXAMPLE 21

1-[4-(Dimethylamino)-2-butynyl]-3-phenyl-2-imidazolidinone

This product, a liquid, was prepared according to Example 1, Part B by substituting 1-phenyl-3-(2-propynyl)-2-imidazolidinone for 1-methyl-3-(2-propynyl)-2-imidazolidinone and dimethylamine for pyrrolidine.

The bulk of the product was converted to the hydrochloride salt; m.p. 199°–202° C.

Anal. Calcd for $C_{15}H_{19}N_3O \cdot HCl$: C, 61.32; H, 6.86; N, 14.30; Cl, 12.07. Found: C, 60.92; H, 6.72; N, 14.21; Cl, 12.20.

EXAMPLE 22

1-Methyl-3-[1-methyl-4-(1-pyrrolidinyl)-2-butynyl]-2-imidazolidinone

Part A. 1-(1-Methyl-2-propynyl)-2-imidazolidinone.

A mixture of ethylenediamine (100 mL) and 3-chloro-1-butyne (19.0 g) was stirred for 18 h at which time the excess ethylenediamine was removed by distillation under reduced pressure. Sodium hydroxide (50 mL of 50% aqueous) was added to the residual oil and the product was extracted with ether (4×150 mL). The ether was washed with saturated sodium chloride solution (2×10 mL) and was then evaporated to give 13.5 g of N-(1-methyl-2-propynyl)ethylene-diamine which was used without further purification.

The bulk of the product (12.5 g) was dissolved in DMF (100 mL) and carbonyldiimidazole (25 g) was added over a period of 10 min. The solution was stirred for 30 min and was then evaporated and the residue was chromatographed on silica gel using chloroform:methanol as the eluant to give 7.8 g of 1-(1-methyl-2-propynyl)-2-imidazolidinone. The product was crystallized from ethyl acetate:Skellysolve B to give 6.3 g, m.p. 90°–92° C.

Anal. Calcd for $C_7H_{10}N_2O$: C, 60.85; H, 7.30; N, 20.28. Found: C, 61.10; H, 7.10; N, 20.35.

Part B. 1-Methyl-3-(1-methyl-2-propynyl)-2-imidazolidinone.

Sodium hydride (1.2 g of 50% in oil) was added at 0° C. to a stirred solution of 1-(1-methyl-2-propynyl)-2-imidazolidinone (2.1 g) in dry THF (50 mL). After 15 min methyl iodide (3.0 mL) was added and the solution was stirred for an additional 30 min. Acetic acid (0.6 mL) and methanol (3 mL) were added and the solvent was removed under reduced pressure and the residual oil was partitioned between ethyl acetate and sodium hydroxide (10 mL of 2N). The ethyl acetate was removed and the crude product was chromatographed on silica gel to give 2.5 g of 1-methyl-3-(1-methyl-2-propynyl)-2-imidazolidinone as an oil.

Part C. 1-Methyl-3-[1-methyl-4-(1-pyrrolidinyl)-2-butynyl]-2-imidazolidinone.

This product was prepared according to Example 1, Part B, by substituting 1-methyl-3-(1-methyl-2-propynyl)-2-imidazolidinone for 1-methyl-3-(2-propynyl)-2-imidazolidinone.

The bulk of the product was converted to the oxalate salt; m.p. 98°–101° C.

Anal. Calcd for $C_{13}H_{21}N_3O \cdot C_2H_2O_4$: C, 55.37; H, 7.13; N, 12.92. Found: C, 55.40; H, 7.53; N, 13.00.

EXAMPLE 23

1-[4-Diethylamino)-2-butynyl]-2-imidazolidinone

This product, a liquid, was prepared according to Example 1, Part B, by substituting diethylamine for pyrrolidine and 1-(2-propynyl)-2-imidazolidinone for 1-methyl-3-(2-propynyl)-2-imidazolidinone.

EXAMPLE 24

1-[4-(Diethylamino)-2-butynyl]-3-methyl-2-imidazolidinone

This product was prepared according to Example 1, Part B, by substituting diethylamine for pyrrolidine.

The bulk of the product was converted to the oxalate salt; m.p. 110°–113° C.

Anal. Calcd for $C_{12}H_{21}N_3O \cdot C_2H_2O_4$: C, 53.66; H, 7.40; N, 13.41. Found: C, 53.78; H, 7.43; N, 13.52.

EXAMPLE 25

1-[4-(1H-Imidazol-1-yl)-2-butynyl]-2-imidazolidinone

This product was prepare according to Example 6 by substituting 1-(4-bromo-2-butynyl)-2-imidazolidinone for 1-(4-bromo-2-butynyl)-1,3-dihydro-3-methyl-2H-imidazol-2-one; m.p. 97°–101° C.

Anal. Calcd for $C_{10}H_{12}N_4O$: C, 58.81; H, 5.92; N, 27.44. Found: C, 59.04; H, 5.99; N, 27.69.

EXAMPLE 26

1-Acetyl-3-[4-(5-methyl-1H-imidazol-1-yl)-2-butynyl]-2-imidazolidinone

This product was prepared according to Example 7 by substituting 1-(4-bromo-2-butynyl)-2-imidazolidinone for 1-(4-bromo-2-butynyl)-1,3-dihydro-3-methyl-2H-imidazol-2-one and was isolated in 27% yield as the first product eluted from a silica gel column; m.p. 93°–95° C.

Anal. Calcd for $C_{13}H_{16}N_4O_2$: C, 59.98; H, 6.20; N, 21.53. Found: C, 59.69; H, 6.29; N, 21.35.

EXAMPLE 27

1-[4-(5-Methyl-1H-imidazol-1-yl)-2-butynyl]-2-imidazolidinone

This product was prepare according to Example 7 by substituting 1-(4-bromo-2-butynyl)-2-imidazolidinone for 1-(4-bromo-2-butynyl)-1,3-dihydro-3-methyl-2H-imidazol-2-one and was isolated in 16% yield as the second product eluted from a silica gel column; m.p. 163°–167° C.

Anal. Calcd for $C_{11}H_{14}N_4O$: C, 60.53; H, 6.47; N, 25.67. Found: C, 60.62; H, 6.51; N, 25.79.

EXAMPLE 28

1-[4-(1H-Imidazol-1-yl)-2-butynyl]-3-methyl-2-imidazolidinone

This product was prepare according to Example 6 by substituting 1-(4-bromo-2-butynyl)-3-methyl-2-imidazolidinone for 1-(4-bromo-2-butynyl)-1,3-dihydro-3-methyl-2H-imidazol-2-one.

The bulk of the product was converted to the oxalate salt; m.p. 132°–134° C.

Anal. Calcd for $C_{11}H_{14}N_4O \cdot C_2H_2O_4$: C, 50.64; H, 5.23; N, 18.18. Found: C, 50.64; H, 5.42; N, 18.14.

EXAMPLE 29

1-Methyl-3-[4-(5-methyl-1H-imidazol-1-yl)-2-butynyl]-2-imidazolidinone

This product was prepared according to Example 7 by substituting 1-(4-bromo-2-butynyl)-3-methyl-2-imidazolidinone for 1-(4-bromo-2-butynyl)-1,3-dihydro-3-methyl-2H-imidazol-2-one.

The bulk of the product was converted to the oxalate salt; m.p. 112°–115° C.

Anal. Calcd for $C_{12}H_{16}N_4O \cdot C_2H_2O_4$: C, 52.17; H, 5.63; N, 17.38. Found: C, 52.52; H, 5.81; N, 17.41.

EXAMPLE 30

1-Ethyl-3-[4-(1-pyrrolidinyl)-2-butynyl]-2-imidazolidinone

This product was prepared according to Example 1, Part B, by substituting 1-ethyl-3-(2-propynyl)-2-imidazolidinone for 1-methyl-3-(2-propynyl)-2-imidazolidinone.

The bulk of the product was converted to the oxalate salt; m.p. 132°–135° C.

Anal. Calcd for $C_{13}H_{21}N_3O \cdot C_2H_2O_4$: C, 55.37; H, 7.13; N, 12.92. Found: C, 55.67; H, 7.16; N, 12.99.

EXAMPLE 31

1-[1-Methyl-4-(1-pyrrolidinyl)-2-butynyl]-2-imidazolidinone

This product was prepared according to Example 1, Part B, by substituting 1-(1-methyl-2-propynyl)-2-imidazolidinone for 1-methyl-3-(2-propynyl)-2-imidazolidinone.

The bulk of the product was converted to the oxalate salt; m.p. 150°–153° C.

Anal. Calcd for $C_{12}H_{19}N_3O \cdot C_2H_2O_4$: C, 54.01; H, 6.80; N, 13.50. Found: C, 53.61; H, 6.97; N, 13.50.

EXAMPLE 32

1-[4-(Dimethylamino)-1-methyl-2-butynyl]-3-methyl-2-imidazolidinone

This product was prepared according to Example 1, Part B, by substituting 1-methyl-3-(1-methyl-2-propynyl)-2-imidazolidinone for 1-methyl-3-(2-propynyl)-2-imidazolidinone and dimethylamine for pyrrolidine.

The bulk of the product was converted to the oxalate salt; m.p. 138°–140° C.

Anal. Calcd for $C_{11}H_{19}N_3O \cdot C_2H_2O_4$: C, 52.16; H, 7.07; N, 14.04. Found: C, 52.23; H, 7.25; N, 14.10.

EXAMPLE 33

1-[4-(Dimethylamino)-2-butynyl]-2-imidazolidinone

This product was prepared according to Example 1, Part B, by substituting 1-(2-propynyl)-2-imidazolidinone for 1-methyl-3-(2-propynyl)-2-imidazolidinone and dimethylamine for pyrrolidine; m.p. 83°–87° C.

Anal. Calcd for $C_9H_{15}N_3O$: C, 59.64; H, 8.34; N, 23.19. Found: C, 59.28; H, 8.26; N, 22.96.

EXAMPLE 34

1-[4-(Diethylamino)-1-methyl-2-butynyl]-3-methyl-2-imidazolidinone

This product, a liquid, was prepared according to Example 1, Part B, by substituting 1-methyl-3-(1-methyl-2-propynyl)-2-imidazolidinone for 1-methyl-3-(2-propynyl)-2-imidazolidinone and diethylamine for pyrrolidine.

The bulk of the product was converted to the oxalate salt; m.p. 105°–108° C.

Anal. Calcd for $C_{13}H_{23}N_3O \cdot C_2H_2O_4$: C, 55.03; H, 7.70; N, 12.84. Found: C, 55.01; H, 7.83; N, 12.90.

EXAMPLE 35

3-[4-(1H-Imidazol-1-yl)-1-methyl-2-butynyl]-1-methyl-2-imidazolidinone

This product was prepare according to Example 6 by substituting 1-(4-bromo-1-methyl-2-butynyl)-3-methyl-2-imidazolidinone for 3-(4-bromo-2-butynyl)-1,3-dihydro-1-methyl-2H-imidazol-2-one; m.p. 89°–92° C.

Anal. Calcd for $C_{12}H_{16}N_4O$: C, 62.05; H, 6.94; N, 24.12. Found: C, 61.95; H, 7.22; N, 24.00.

EXAMPLE 36

1,3-Dihydro-1-methyl-3-[4-(1-pyrrolidinyl)-2-butynyl]-2H-imidazol-2-one

This product, a liquid, was prepared according to Example 1, Part B by substituting 1,3-dihydro-1-methyl-3-(2-propynyl)-2H-imidazol-2-one for 1-methyl-3-(2-propynyl)-2-imidazolidinone.

The bulk of the product was converted to the hemifumarate salt; m.p. 125°–128° C.

Anal. Calcd for $C_{12}H_{17}N_3O \cdot \frac{1}{2}C_4H_4O$: C, 60.63; H, 6.91; N, 15.15. Found: C, 60.30; H, 7.06; N, 15.09.

EXAMPLE 37

1,3-Dihydro-1-[4-(dimethylamino)-2-butynyl]-3-methyl-2H-imidazol-2-one

This product, a liquid, was prepared according to Example 1, Part B by substituting 1,3-dihydro-1-methyl-3-(2-propynyl)-2H-imidazol-2-one for 1-methyl-3-(2-propynyl)-2-imidazolidinone and dimethylamine for pyrrolidine.

The bulk of the product was converted to the oxalate salt; m.p. 102°–114° C.

Anal. Calcd for $C_{10}H_{15}N_3O \cdot C_2H_2O_4$: C, 50.88; H, 6.05; N, 14.83. Found: C, 50.13; H, 6.20; N, 14.42.

EXAMPLE 38

1,3-Dihydro-1-[4-(1-pyrrolidinyl)-2-butynyl]-2H-imidazol-2-one

This product was prepared according to Example 1, Part B by substituting 1,3-dihydro-1-(2-propynyl)-2H-imidazol-2-one for 1-methyl-3-(2-propynyl)-2-imidazolidinone; m.p. 99°–102° C.

Anal. Calcd for $C_{11}H_{15}N_3O$: C, 64.36; H, 7.37; N, 20.47. Found: C, 64.29; H, 7.30; N, 20.74.

EXAMPLE 39

1,3-Dihydro-1-methyl-3-[1-methyl-4-(1-pyrrolidinyl)-2-butynyl]-2H-imidazol-2-one Part A. 2,2-diethoxy-N-(1-methyl-2-propynyl)ethylamine.

A mixture of 3-chloro-2-butyne (22.0 g of 80% solution in ether, 0.2 mol) and aminoacetaldehyde diethyl acetal (53.3 g, 0.4 mol) was heated to 110° C. for 1.5 h. The solution was cooled, dissolved in chloroform (100 mL), and chromatographed on silica gel to give 13.7 g of 2,2-diethoxy-N-(1-methyl-2-propynyl)ethylamine.

Part B. 1,3-dihydro-1-methyl-3-(1-methyl-2-propynyl)-2H-imidazol-2-one.

Methyl isocyanate (4.6 g, 0.081 mol) was added to a stirred solution of 2,2-diethoxy-N-(2-propynyl)ethylamine (13.7 g, 0.074 mol) in ether (150 mL). After 30 min the ether was evaporated and the residue was dissolved in water (150 mL), oxalic acid (6.7 g) was added, and the solution was heated at 50° C. for 30 min. The solution was then concentrated to 20 mL and neutralized with 4N NaOH solution, and extracted with ethyl acetate (4×150 mL). The ethyl acetate was evaporated and the residue was chromatographed on silica gel to give 9.6 g of product as an oil.

Part C. 1,3-Dihydro-1-methyl-3-[1-methyl-4-(1-pyrrolidinyl)-2-butynyl]-2H-imidazol-2-one.

This product, a liquid, was prepared according to Example 1, Part B by substituting 1,3-dihydro-1-methyl-3-(1-methyl-2-propynyl)-2H-imidazol-2-one for 1-methyl-3-(2-propynyl)-2-imidazolidinone.

The bulk of the product was converted to the oxalate salt; m.p. 130°–133° C.

Anal. Calcd for $C_{13}H_{19}N_3O \cdot C_2H_2O_4$: C, 55.72; H, 6.55; N, 13.00. Found: C, 55.72; H, 6.82; N, 12.99.

EXAMPLE 40

1,3-Dihydro-1-methyl-3-[4-(dimethylamino)-1-methyl-2-butynyl]-2H-imidazol-2-one

This product, a liquid, was prepared according to Example 1, Part B by substituting 1,3-dihydro-1-methyl-3-(1-methyl-2-propynyl)-2H-imidazol-2-one for 1-methyl-3-(2-propynyl)-2-imidazolidinone and dimethylamine for pyrrolidine.

The bulk of the product was converted to the oxalate salt; m.p. 113°–117° C.

Anal. Calcd for $C_{11}H_{17}N_3O \cdot C_2H_2O_4$: C, 52.51; H, 6.44; N, 14.13. Found: C, 52.40; H, 6.66; N, 14.10.

EXAMPLE 41

3-[4-(Dimethylamino)-2-butynyl]-1-methyl-2,4-imidazolidinedione

This product, a liquid, was prepared according to Example 1 by substituting 1-methylhydantoin for 1-methyl-2-imidazolidinone and dimethylamine for pyrrolidine.

The bulk of the product was converted to the methanesulfonate salt; m.p. 127°–30° C.

Anal. Calcd for $C_{10}H_{15}N_3O_2 \cdot CH_4O_3S$: C, 43.27; H, 6.27; N, 13.76; S, 10.50. Found: C, 43.26; H, 6.19; N, 13.76; S, 10.82.

EXAMPLE 42

Tetrahydro-1-methyl-3-[4-(1-pyrrolidinyl)-2-butynyl]-2(1H)-pyrimidinone

This product, a liquid, was prepared according to Example 1 by substituting tetrahydro-1-methyl-2(1H)-pyrimidinone for 1-methyl-2-imidazolidinone.

The bulk of the product was converted to the oxalate salt; m.p. 135°–138° C.

Anal. Calcd for $C_{13}H_{21}N_3O \cdot C_2H_2O_4$: C, 55.37; H, 7.13; N, 12.92. Found: C, 55.16; H, 7.22; N, 12.85.

EXAMPLE 43

3-Methyl-1-[4-(1-pyrrolidinyl)-2-butynyl[-2,4-imidazolidinedione

This product, a liquid, was prepared according to Example 1, Part B, by substituting 1-(2-propynyl)-3-methylhydantoin for 1-methyl-3-(2-propynyl)-2-imidazolidinone.

The bulk of the product was converted to the oxalate salt; m.p. 88°–108° C.

Anal. Calcd for $C_{12}H_{17}N_3O_2 \cdot C_2H_2O_4$: C, 51.68; H, 5.89; N, 12.92. Found: C, 50.93; H, 5.97; N, 12.64.

EXAMPLE 44

1-Methyl-3-[4-(1-pyrrolidinyl)-2-butynyl]-2,4-imidazolidinedione

This product, a liquid, was prepared according to Example 1 by substituting 1-methylhydantoin for 1-methyl-2-imidazolidinone.

The bulk of the product was converted to the oxalate salt; m.p. 99°–101° C.

Anal. Calcd for $C_{12}H_{17}N_3O_2 \cdot C_2H_2O_4$: C, 51.68; H, 5.89; N, 12.92. Found: C, 51.58; H, 5.95; N, 12.64.

EXAMPLE 45

Part A. (R)-t-Butyl 2-(hydroxymethyl)-1-pyrrolidinecarboxylate.

Di-t-butyl dicarbonate (65.5 g, 0.30 mol) was added at 0° C. to a stirred solution of (R)-2-pyrrolidinemethanol (25.0 g, 0.25 mol) in THF (350 mL). After 15 min the solution was allowed to warm to room temperature and was stirred for an additional 1 hr. The THF was removed under reduced pressure and the residual oil was dissolved in chloroform and chromatographed on silica gel to give 40.6 g (81%) of product as an oil. An analytical sample was crystallized from ether; m.p. 57°-60° C. [α]$_D$ +55° (c 0.71, MeOH).

Anal. Calcd. for C$_{10}$H$_{19}$NO$_3$: C, 59.67; H, 9.52; N, 6.96. Found: C, 59.14; H, 9.42; N, 6.80.

Part B. (S)-t-Butyl 2-(hydroxymethyl)-1-pyrrolidinecarboxylate.

Following the above procedure, but substituting (S)-prolinol for (R)-prolinol there was obtained 43.5 g (86%) of pure product as an oil. An analytical sample was crystallized from ether; m.p. 62°-64° C. [α]$_D$ −50° C. (c 0.77, CHCl$_3$).

Anal. Calcd. for C$_{10}$H$_{19}$NO$_3$: C, 59.67; H, 9.52; N, 6.96. Found: C, 59.57; H, 9.34; N, 6.96.

EXAMPLE 46

Part A. (R)-t-Butyl 2-formyl-1-pyrrolidinecarboxylate.

Oxalyl chloride (12.0 ml, 0.14 mol) was added dropwise with stirring to methylene chloride (200 mL) at −78° C., under nitrogen. Ten min. after addition was complete, DMSO (20 mL) was slowly added and stirring was continued for an additional 10 min. (R)-t-Butyl 2-(hydroxymethyl)-1-pyrrolidinecarboxylate (15.0 g, 0.075 mol) in methylene chloride was added to the stirred solution and after 30 min triethylamine (56 mL) was added. The solution was held at −78° C. for 30 min. and was then allowed to warm to room temperature. Water (100 mL) was added, the phases separated, and the aqueous phase reextracted with methylene chloride (200 mL). The combined organic phases were washed with water (30 mL), evaporated, and the residual oil was chromatographed on silica gel using ethyl acetate:Skellysolve B (1:2) as eluant to give 14.2 g (95%) of product.

Part B. (S)-t-Butyl 2-formyl-1-pyrrolidinecarboxylate.

This liquid product was obtained in 98% yield following the above procedure by substituting (S)-t-Butyl 2-(hydroxymethyl)-1-pyrrolidinecarboxylate for (R)-t-Butyl 2-(hydroxymethyl)-1-pyrrolidinecarboxylate.

EXAMPLE 47

Part A. (R)-t-Butyl 2-(2,2-dibromoethenyl)-1-pyrrolidinecarboxylate.

Carbon tetrabromide (49.2 g, 0.15 mol) in methylene chloride (150 mL) was added at 0° C. to a stirred solution of triphenyl phosphine (78.2 g, 0.30 mol) in methylene chloride (600 mL) under nitrogen. The solution was stirred at 0° C. for 1 hr. and (R)-t-butyl 2-formyl-1-pyrrolidinecarboxylate (21.9 g, 0.10 mol) was added. After 30 min. a solution of sodium carbonate (75 g, 0.75 mol) in water (300 mL) was added. The phases were separated and the aqueous phase was reextracted with methylene chloride (200 mL). The organic phase was washed with water (40 mL), and the majority of solvent was removed under reduced pressure leaving the material in a minimum of methylene chloride. Ethyl acetate (500 mL) was added and the resulting precipitate of triphenylphosphine oxide was filtered off. The mother liquors were evaporated and filtered repeatedly to remove additional triphenylphosphine oxide. The residual solid in ethyl acetate was then concentrated and applied to a silica gel column. Elution with ethyl acetate:Skellysolve B (1:10) gave 31.6 g (91%) of product. This was crystallized from petroleum ether to give 25.8 g of product, m.p. 64°-67° C. The analytical sample was recrystallized from ethyl acetate:Skellysolve B. [α]$_D$ −21° (c 0.81, MeOH).

Anal. Calcd. for C$_{11}$H$_{17}$Br$_2$NO$_2$: C, 37.21; H, 4.83; N, 3.95; Br, 45.01. Found: C, 36.95; H, 4.85; N, 3.78; Br, 45.08.

Part B. (S)-t-Butyl 2-(2,2-dibromoethenyl)-1-pyrrolidinecarboxylate.

This compound was prepared in 74% yield following the above procedure by substituting (S)-t-butyl 2-formyl-1-pyrrolidinecarboxylate for (R)-t-butyl 2-formyl-1-pyrrolidinecarboxylate; m.p. 65°-67° C. [α]$_D$ +20° (c 0.88, MeOH).

Anal. Calcd. for C$_{11}$H$_{17}$Br$_2$NO$_2$: C, 37.21; H, 4.83; N, 3.95; Br, 45.01. Found: C, 37.25; H, 4.85; N, 3.95; Br, 45.75.

EXAMPLE 48

Part A. (R)-t-Butyl 2-ethynyl-1-pyrrolidinecarboxylate.

Butyl lithium (48 mL, 0.08 mol) was added at −78° C. to a stirred solution of (R)-t-butyl 2-(2,2-dibromoethenyl)-1-pyrrolidinecarboxylate (14.2 g, 0.04 mol) in dry THF (300 mL). The color turned to dark yellow. After 15 min. methanol (10 mL) and ethyl acetate (10 mL) were added and the solution was allowed to warm to room temperature. The solvent was removed and the residue was partitioned between ethyl acetate and water. The ethyl acetate phase was concentrated and applied to a silica gel column. Elution with ethyl acetate:Skellysolve B (1:10) gave 6.9 g (88%) of product as a yellow oil.

Part B. (S)-t-Butyl 2-ethynyl-1-pyrrolidinecarboxylate.

This product was prepared in 84% yield using the above procedure by substituting (S)-t-butyl 2-(2,2-dibromoethenyl)-1-pyrrolidinecarboxylate for (R)-t-butyl 2-(2,2-dibromoethenyl)-1-pyrrolidinecarboxylate.

EXAMPLE 49

Part A. (R)-t-Butyl 2-[3-(1-pyrrolidinyl)-1-propynyl]-1-pyrrolidine-carboxylate.

A mixture of (R)-t-butyl 2-ethynyl-1-pyrrolidinecarboxylate (4.2 g, 0.02 mol), pyrrolidine (2.1 g, 0.03 mol), paraformaldehyde (0.9 g, 0.03 mol), and cuprous chloride (30 mg), in dioxane (30 mL) was stirred at 70° C. for 40 min. The dioxane was removed and the residual oil was dissolved in chloroform and chromatographed on silica gel using 2 to 5% methanol:chloroform as eluant to give 3.8 g (88%) of pure product as an oil. [a]$_D$ +129° (c 0.51, MeOH).

An aliquot of the product was converted to the oxalate salt, m.p. 78° C. (dec) from methanol:ether. [α]$_D$ +95° (c 0.91, MeOH).

Anal. Calcd. for C$_{16}$H$_{26}$N$_2$O$_2$.C$_2$H$_2$O$_4$: C, 58.68; H, 7.66; N, 7.60. Found: C, 58.52; H, 7.81; N, 7.43.

Part B. (S)-t-Butyl 2-[3-(1-pyrrolidinyl)-1-propynyl]-1-pyrrolidinecarboxylate.

This compound was obtained as an oil using Example 49, Part A but substituting (S)-t-butyl 2-ethynyl-1-pyrrolidinecarboxylate for (R)-t-butyl 2-ethynyl-1-pyrrolidinecarboxylate.

Part C. (R)-t-Butyl 2-[3-(dimethylamino)-1-propynyl]-1-pyrrolidinecarboxylate.

This compound was obtained as an oil using Example 49, Part A but substituting dimethylamine for pyrrolidine.

A portion of the product was converted to the oxalate salt; m.p. 140°-143° C. from methanol:ether. [α]$_D$ +109° (c 0.86, MeOH); [α]$_D$ +86° (c 0.86, DMSO).

Anal. Calcd. for $C_{14}H_{24}N_2O_2 \cdot C_2H_2O_4$: C, 56.12; H, 7.65; N, 8.18. Found: C, 55.88; H, 7.94; N, 8.05.

Part D. (S)-t-Butyl 2-[3-(dimethylamino)-1-propynyl]-1-pyrrolidinecarboxylate.

This compound was obtained as an oil using Example 49, Part A but substituting (S)-t-butyl 2-ethynyl-1-pyrrolidinecarboxylate for (R)-t-butyl 2-ethynyl-1-pyrrolidinecarboxylate and dimethylamine for pyrrolidine.

A portion of the product was converted to the oxalate salt; m.p. 140°-143° C. from methanol:ether. $[\alpha]_D$ −110° (c 0.76, MeOH); $[\alpha]_D$ −87° (c 0.90, DMSO).

Anal. Calcd. for $C_{14}H_{24}N_2O_2 \cdot C_2H_2O_4$: C, 56.12; C, 7.65; N, 8.18. Found: C, 56.17; H, 7.83; N, 8.44.

EXAMPLE 50

Part A. (R)-1-[3-(2-pyrrolidinyl)-2-propynyl]pyrrolidine.

(R)-t-Butyl 2-[3-(1-pyrrolidinyl)-1-propynyl]-1-pyrrolidinecarboxylate (11.06 g, 0.039 mol) was dissolved in methanolic HCl (200 mL) and stirred at room temperature for 2 hr. The reaction was evaporated under house and high vacuum to give a beige solid which was recrystallized from methanol:ether to give 9.5 g of product. The analytical sample was recrystallized from methanol:ether; m.p. 214°-216° C. $[\alpha]_D$ +21° (c 0.55, MeOH).

Anal. Calcd. for $C_{11}H_{18}N_2 \cdot 2HCl$: C, 52.59; H, 8.03; N, 11.15; Cl, 28.23. Found: C, 52.91; H, 8.01; N, 11.21; Cl, 28.44.

Part B. (S)-1-[3-(2-pyrrolidinyl)-2-propynyl]pyrrolidine.

This compound was obtained as the dihydrochloride salt following Example 50, Part A by substituting (S)-t-butyl (1-pyrrolidinyl)-1-propynyl]-1-pyrrolidinecarboxylate for (R)-t-butyl 2-[3-(1-pyrrolidinyl)-1-propynyl]-1-pyrrolidinecarboxylate, a white hygroscopic powder, m.p. 208°-211° C. $[\alpha]_D$ −23° (c 0.75, MeOH). Recrystallization of the mother liquor gave an additional 26% of product.

Part C. (R)-N,N-dimethyl-3-(2-pyrrolidinyl)-2-propyn-1-amine.

This compound was prepared in 91% yield according to Example 50, Part A by substituting (R)-t-butyl 2-[3-(1-dimethylamino)-1-propynyl]-1-pyrrolidinecarboxylate for (R)-t-butyl 2-[3-(1-pyrrolidinyl)-1-propynyl]-1-pyrrolidinecarboxylate and was obtained as the dihydrochloride salt, a hygroscopic solid, m.p. 194°-197° C. $[\alpha]_D$ +23° (c 1.00, MeOH).

Anal. Calcd. for $C_9H_{16}N_2 \cdot 2HCl$: C, 48.00; H, 8.06; N, 12.44; Cl, 31.49. Found: C, 47.03; H, 8.17; N, 12.15; Cl, 30.89.

Part D. (S)-N,N-dimethyl-3-(2-pyrrolidinyl)-2-propyn-1-amine.

This compound was prepared in 91% yield according to Example 50, Part A but substituting (S)-t-butyl 2-[3-(dimethylamino)-1-propynyl]-1-pyrrolidinecarboxylate for (R)-t-butyl 2-[3-(1-pyrrolidinyl)-1-propynyl]-1-pyrrolidinecarboxylate and was obtained as the dihydrochloride salt, a hygroscopic solid, m.p. 182°-190° C. $[\alpha]_D$ −23° (c 1.00, MeOH).

Anal. Calcd. for $C_9H_{16}N_2 \cdot 2HCl$: C, 48.00; H, 8.06; N, 12.44; Cl, 31.49. Found: C, 46.38; H, 7.87; N, 11.81; Cl, 30.60.

Example 51

Part A. (R)-1-Acetyl-2-[3-(1-pyrrolidinyl)-1-propynyl]pyrrolidine.

Acetic anhydride (1.1 g, 0.011 mol) was added to a stirred solution of (R)-1-[3-(2-pyrrolidinyl)-2-propynyl]pyrrolidine (2.51 g, 0.01 mol) in aqueous sodium hydroxide (20 mL of 1.0N). After 15 min. the product was extracted into ethyl acetate, the solvent was evaporated and the residual oil was chromatographed on silica gel using methanol:chloroform as the eluant to give 2.16 g of product. $[\alpha]_D$ +135° (c 1.00, MeOH).

Part B. (S)-1-Acetyl-2-[3-(1-pyrrolidinyl)-1-propynyl]pyrrolidine.

This compound was obtained following Example 51, Part A but substituting (S)-1-[3-(2-pyrrolidinyl)-2-propynyl]pyrrolidine for (R)-1-[3-(2-pyrrolidinyl)-2-propynyl]pyrrolidine.

Part C. (R)-1-Acetyl-2-[3-(dimethylamino)-1-propynyl]pyrrolidine.

This compound was obtained following Example 51, Part A but substituting (R)-N,N-(dimethyl-3-(2-pyrrolidinyl)-2-propyn-1-amine for (R)-1-[3-(2-pyrrolidinyl)-2-propynyl]pyrroline. $[\alpha]_D$ +154° (c 1.00, MeOH).

The bulk of the material was converted to the oxalate salt, m.p. 75°-79° C. $[\alpha]_D$ +115° (c 1.01, MeOH).

Anal. Calcd. for $C_{11}H_{18}N_2O \cdot C_2H_2O_4$: C, 54.91; H, 7.09; N, 9.86. Found: C, 53.26; H, 7.00; N, 9.42.

Part D. (S)-1-Acetyl-2-[3-(dimethylamino)-1-propynyl]pyrrolidine.

This compound was obtained following Example 51, Part A but substituting (S)-N,N-dimethyl-3-(2-pyrrolidinyl)-2-propyn-1-amine for (R)-1-[3-(2-pyrrolidinyl)-2-propynyl]pyrrolidine.

The bulk of the material was converted to the oxalate salt, m.p. 72°-75° C. $[\alpha]_D$ −113° (c 1.01, MeOH).

Anal. Calcd. for $C_{11}H_{18}N_2O \cdot C_2H_2O_4$: C, 54.91; H, 7.09; N, 9.86. Found: C, 54.17; H, 7.24; N, 9.69.

Part E. (R)-N,N-Dimethyl 2-[3-(1-pyrrolidinyl)-1-propynyl]-1-pyrrolidinecarboxamide.

This compound was obtained following Example 51, Part A but substituting dimethyl carbamoyl chloride for acetic anhydride.

The bulk of the material was converted to the oxalate salt, m.p. 84°-87° C. $[\alpha]_D$ +38° (c 0.55, MeOH).

Anal. Calcd. for $C_{14}H_{23}N_3O \cdot C_2H_2O_4$: C, 56.62; H, 7.43; N, 12.38. Found: C, 56.53; H, 7.72; N, 12.54.

Part F. (S)-N,N-Dimethyl 2-[3-(1-pyrrolidinyl)-1-propynyl]-1-pyrrolidinecarboxamide.

This compound was obtained following Example 51, Part A but substituting (S)-1-[3-(2-pyrrolidinyl)-2-propynyl]pyrrolidine for (R)-1-[3-(2-pyrrolidinyl)-2-propynyl]pyrrolidine and dimethyl carbamoyl chloride for acetic anhydrode. $[\alpha]_D$ −78° (c 1.13, MeOH).

Anal. Calcd. for $C_{14}H_{23}N_3O$: C, 67.43; H, 9.30; N, 16.85. Found: C, 67.61; H, 9.51; N, 16.60.

Part G. (R)-N-Methyl 2-[3-(1-pyrrolidinyl)-1-propynyl]-1-pyrrolidinecarboxamide.

This compound was obtained following Example 51, Part A but substituting methyl isocyanate for acetic anhydride.

The bulk of the material was converted to the oxalate salt, m.p. 120°-128° C. $[\alpha]_D$ +82° (c 0.73, MeOH).

Anal. Calcd. for $C_{13}H_{21}N_3O \cdot C_2H_2O_4$: C, 55.37; H, 7.13; N, 12.92. Found: C, 54.25; H, 7.15; N, 12.49.

Part H. (R)-2-[3-(1-pyrrolidinyl)-1-propynyl]-1-pyrrolidinecarboxamide.

This compound was obtained following Example 51, Part A but substituting potassium cyanate for acetic anhydride; m.p. 117°-122° C. [α]$_D$ +125° (c 0.54, MeOH).

Anal. Calcd. for C$_{12}$H$_{19}$N$_3$O: C, 65.12; H, 8.65; N, 18.99. Found: C, 64.08; H, 8.65; N, 18.99.

Part I. (R)-2-[3-(1-pyrrolidinyl)-1-propynyl]-1-pyrrolidinecarbonitrile.

This compound was obtained following Example 51, Part A but substituting cyanogen bromide for acetic anhydride; m.p. 117°-122° C. [α]$_D$ +126° (c 0.59, MeOH).

The bulk of the material was converted to the oxalate salt.

Anal. Calcd. for C$_{12}$H$_{17}$N$_3$·C$_2$H$_2$O$_4$: C, 57.32; H, 6.53; N, 14.33. Found: C, 57.25; H, 6.68; N, 14.47.

Part J. (R)-Methyl 2-[3-(1-pyrrolidinyl)-1-propynyl]-1-pyrrolidinecarboxylate.

This compound was obtained following Example 51, Part A but substituting methyl chloroformate for acetic anhydride.

The bulk of the material was converted to the p-toluenesulfonate salt, m.p. 117°-120° C. [α]$_D$ +81° (0.87, MeOH).

Anal. Calcd. for C$_{13}$H$_{20}$N$_2$O$_2$·C$_7$H$_8$O$_3$S: C, 58.80; H, 6.91; N, 6.86; S, 7.85. Found: C, 58.90; H, 7.17; N, 7.02; S, 7.86.

Part K. (S)-Methyl 2-[3-(1-pyrrolidinyl)-1-propynyl]-1-pyrrolidinecarboxylate.

This compound was obtained following Example 51, Part A but substituting (S)-1-[3-(2-pyrrolidinyl)-2-propynyl]pyrrolidine for (R)-1-[3-(2-pyrrolidinyl)-2-propynyl]pyrrolidine and methyl chloroformate for acetic anhydride.

The bulk of the material was converted to the p-toluenesulfonate salt, m.p. 117°-120° C. [α]$_D$ −81° (c 0.71, MeOH).

Anal. Calcd. for C$_{13}$H$_{20}$N$_2$O$_2$·C$_7$H$_8$O$_3$S: C, 58.80; H, 6.91; N, 6.86; S, 7.85. Found: C, 58.75; H, 7.02; N, 6.78; S, 7.85.

Part L. (R)-Ethyl 2-[3-(1-pyrrolidinyl)-1-propynyl]-1-pyrrolidinecarboxylate.

This compound was obtained following Example 51, Part A but substituting ethyl chloroformate for acetic anhydride.

The bulk of the material was converted to the oxalate salt, m.p. 102°-104° C. [α]$_D$ +100° (c 0.59, MeOH).

Anal. Calcd. for C$_{14}$H$_{22}$N$_2$O$_2$·C$_2$H$_2$O$_4$: C, 56.46; H, 7.11; N, 8.23. Found: C, 53.64; H, 6.42; N, 7.61.

FORMULAS

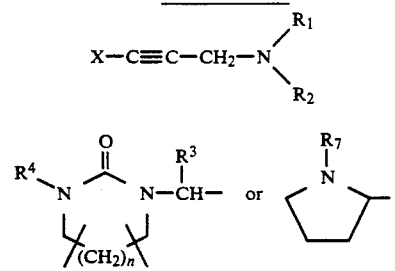

I

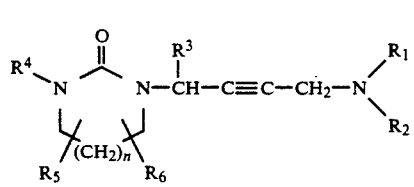

X i

-continued
FORMULAS

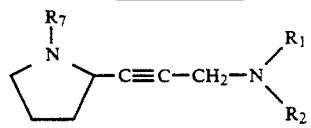

ii

Scheme 1
Synthesis of Imidazolidinone Intermediates

Method A

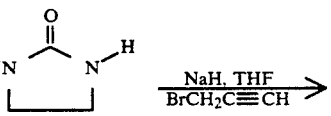

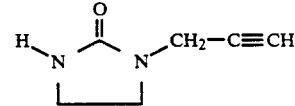

+

II

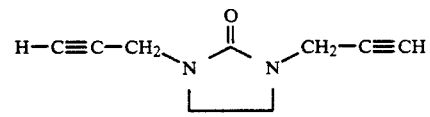

Method B

Cl—CH$_2$CH$_2$—N═C═O

+   $\xrightarrow{\text{THF}}_{0°\text{ C.}}$

H$_2$N—CH$_2$—C≡C—H

III

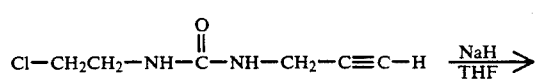

II

Method C

RNH—CH$_2$CH$_2$—NH$_2$ $\xrightarrow{\text{CDI}}_{\text{THF}}$

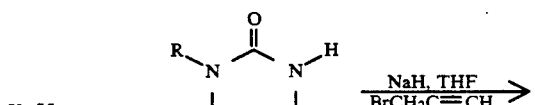

IV

Method D

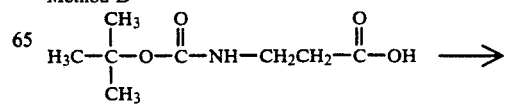

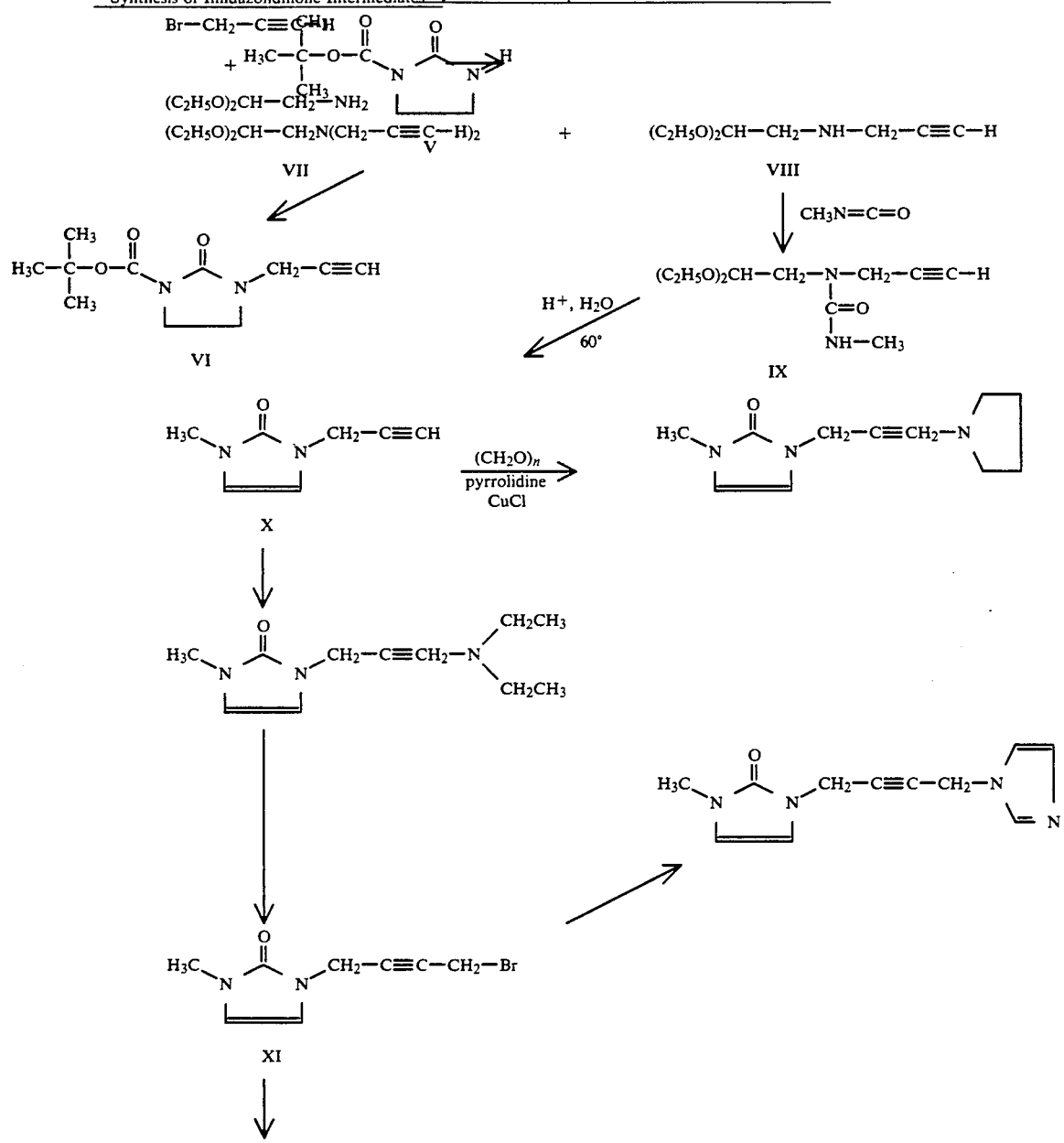

-continued
Scheme 2
Synthesis of Example 36 and Related Imidazolones
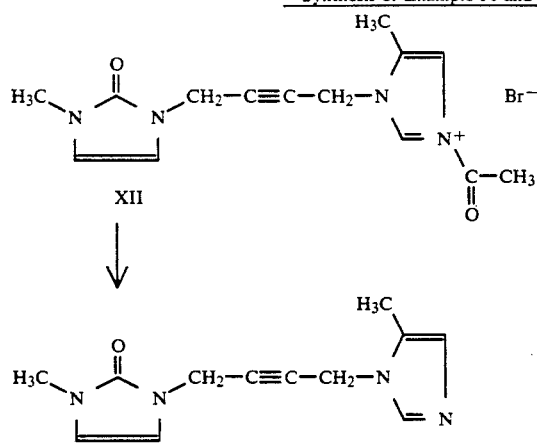
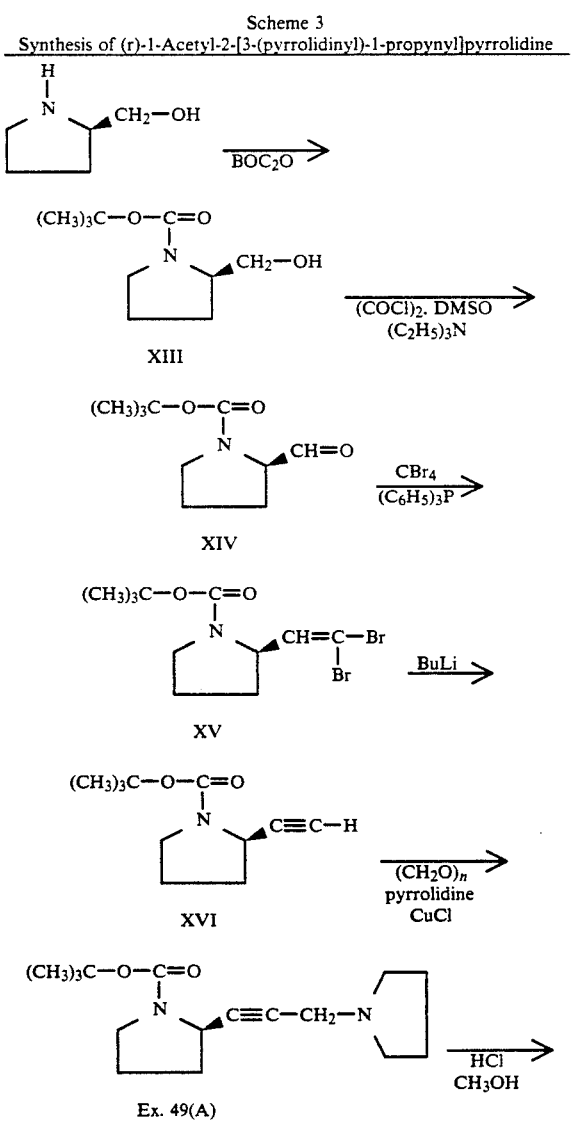
-continued
Scheme 3
Synthesis of (r)-1-Acetyl-2-[3-(pyrrolidinyl)-1-propynyl]pyrrolidine
| TABLE 1 | | | | |
|---|---|---|---|---|
| | CNS Id (ED$_{50}$ mg/kg) HCl | CNS Cholinergic Receptor Binding Assays | Oxot. Antagonist | |
| Compound Number | Writh. Protect | K$_1$ (nM) QNB | K$_1$ (nM) Oxotremorine | Tremor |
| 1 | .2 | 180 | 2.70 | >3 |
| 8 | 25 | 2200 | 130 | >100 |
| 9 | 2.2 | 800 | 13 | >3 |
| 10 | >13 | 180 | 4.5 | >10 |
| 11 | >50 | 4700 | 160 | >100 |
| 12 | >50 | — | 820 | >100 |
| 13 | 12.5 | — | >10000 | >100 |
| 14 | >25 | 2300 | 200 | >30 |
| 15 | >13 | 1000 | 140 | >10 |
| 16 | 25 | 1000 | 290 | >100 |
| 17 | >25 | 2700 | 810 | >100 |
| 18 | 25 | 820 | 180 | >30 |
| 19 | >13 | 20 | 4 | 6.6 |
| 20 | >25 | 170 | 69 | >30 |
| 21 | >50 | >10000 | 840 | >100 |
| 22 | — | 130 | 13 | 37 |
| 23 | — | >10000 | 425 | >100 |
| 24 | — | >10000 | 132 | >100 |
| 25 | — | >10000 | 62 | >100 |
| 26 | — | >10000 | 147 | 45 |
| 27 | — | >10000 | 138 | >100 |
| 28 | — | 1868 | 2 | >100 |
| 29 | — | 381 | 9 | >100 |
| 30 | — | >10000 | 697 | >30 |
| 31 | — | 135 | 15 | >30 |
| 32 | — | >10000 | 33 | >100 |
| 33 | — | >10000 | 43 | >100 |

TABLE 1-continued

| Compound Number | CNS Id (ED$_{50}$ mg/kg) HCl Writh. Protect | CNS Cholinergic Receptor Binding Assays K$_1$ (nM) QNB | Oxot. Antagonist K$_1$ (nM) Oxotremorine | Tremor |
|---|---|---|---|---|
| 34 | — | 1980 | 165 | >100 |
| 35 | — | 4009 | 120 | >100 |

TABLE 2

| Compound Number | CNS Id (ED$_{50}$ mg/kg) HCl Writh. Protect | CNS Cholinergic Receptor Binding Assays K$_1$ (nM) QNB | Oxot. Antagonist K$_1$ (nM) Oxotremorine | Tremor |
|---|---|---|---|---|
| 4 | — | >10000 | 563 | >100 |
| 6 | — | >10000 | 35 | >100 |
| 7 | — | 614 | 39 | >100 |
| 36 | 1.3 | 510 | 7 | >10 |
| 37 | — | >10000 | 37 | >100 |
| 38 | — | >10000 | 33 | >2 |
| 39 | — | 88 | 9 | >30 |
| 40 | — | >10000 | 136 | >100 |

TABLE 3

| Compound Number | CNS Id (ED$_{50}$ mg/kg) HCl Writh. Protect | CNS Cholinergic Receptor Binding Assays K$_1$ (nM) QNB | Oxot. Antagonist K$_1$ (nM) Oxotremorine | Tremor |
|---|---|---|---|---|
| 41 | — | >10000 | 86 | — |
| 42 | — | 1581 | 229 | >30 |
| 43 | — | >10000 | 364 | >100 |
| 44 | — | 8712 | 20 | >30 |

TABLE 4

| Compound Number | CNS Id (ED$_{50}$ mg/kg) HCl Writh. Protect | CNS Cholinergic Receptor Binding Assays K$_1$ (nM) QNB | Oxot. Antagonist K$_1$ (nM) Oxotremorine | Tremor |
|---|---|---|---|---|
| 49A | 13 | 430 | 20 | 100 |
| 49C | >50 | >10000 | 44 | >100 |
| 50A | — | 4800 | 260 | >100 |
| 50C | >50 | >1000 | 970 | >100 |
| 51A | >50 | 120 | — | 3 |
| 51C | >50 | >10000 | 130 | >100 |
| 51E | >50 | 43 | 12 | 25 |
| 51G | >50 | >10000 | 240 | >100 |
| 51H | >50 | >10000 | 440 | >100 |
| 51I | 25 | >10000 | 310 | >30 |
| 51J | 11 | 460 | 57 | >100 |
| 51L | >50 | 760 | 50 | >100 |

TABLE 5

| Compound Number | CNS Id (ED$_{50}$ mg/kg) HCl Writh. Protect | CNS Cholinergic Receptor Binding Assays K$_1$ (nM) QNB | Oxot. Antagonist K$_1$ (nM) Oxotremorine | Tremor |
|---|---|---|---|---|
| 49B | >50 | >10000 | 3500 | >100 |
| 50B | — | >10000 | 1300 | — |
| 50D | >50 | >10000 | >10000 | >100 |
| 51B | — | 2300 | 370 | >30 |
| 51D | >50 | >10000 | >10000 | >100 |
| 51F | >50 | 2000 | 460 | >100 |
| 51K | >50 | 220 | 130 | 97 |

I Claim:

1. A compound of the following structural formula I:

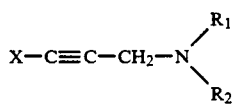

or a therapeutically acceptable salt thereof;
wherein $R_1$ and $R_2$ are hydrogen, methyl, ethyl or joined to form an azetidine, pyrrolidine or piperidine ring which can be substituted with a methyl or ethyl group;
wherein X is

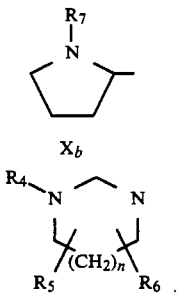

wherein $R_7$ is hydrogen, $C_1$-$C_6$ alkyl, $C_1$-$C_6$ alkylcarbonyl, $C_1$-$C_6$ alkoxycarbonyl, amminocarbonyl, $C_1$-$C_6$ alkylaminocarbonyl, di-$C_1$-$C_6$ alkylaminocarbonyl or cyano.

2. The compound of claim 1 wherein $R_1$ and $R_2$ are dimethylamine or are joined to form a pyrrolidine and $R_7$ is $C_1$-$C_6$ alkylcarbonyl, $C_1$-$C_6$ alkoxycarbonyl or di-$C_1$-$C_6$ alkylaminocarbonyl.

3. The compound of claim 2 which is
a. (R)-t-Butyl 2-[3-(1-pyrrolidinyl)-1-propynyl]-1-pyrrolidine-carboxylate;
b. (R)-t-Butyl 2-[3-(dimethylamino)-1-propynyl]-1-pyrrolidine-carboxylate;
c. (R)-1-Acetyl-2-[3-(1-pyrrolidinyl)-1-propynyl]pyrrolidine;
d. (R)-1-Acetyl-2-[3-(dimethylamino)-1-propynyl]-pyrrolidine;
e. (R)-N,N-Dimethyl 2-[3-(1-pyrrolidinyl)-1-propynyl]-1-pyrrolidine-carboxamide;
f. (R)-Methyl 2-[3-(1-pyrrolidinyl)-1-propynyl]-1-pyrrolidine-carboxylate; or
g. (R)-Ethyl 2-[3-(1-pyrrolidinyl)-1-propynyl]-1-pyrrolidine-carboxylate.

* * * * *